United States Patent
Geis et al.

(10) Patent No.: US 6,413,781 B1
(45) Date of Patent: Jul. 2, 2002

(54) THERMOPHORETIC PUMP AND CONCENTRATOR

(75) Inventors: Michael W. Geis; Roderick R. Kunz, both of Acton; Margaret B. Stern, Sudbury, all of MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 09/287,591

(22) Filed: Apr. 6, 1999

(51) Int. Cl.[7] ......................... G01N 25/00; B01D 17/00

(52) U.S. Cl. ...................... 436/178; 436/177; 436/157; 210/767; 210/774; 210/775; 210/149; 210/176; 422/101

(58) Field of Search ................................ 436/177, 178, 436/157; 210/767, 774, 775, 149, 176; 422/101

(56) References Cited

U.S. PATENT DOCUMENTS

| | | | | |
|---|---|---|---|---|
| 2,521,112 A | * | 9/1950 | Beams | 210/52.5 |
| 2,541,071 A | * | 2/1951 | Jones et al. | 260/97.7 |
| 3,449,938 A | | 6/1969 | Giddings | |
| 4,029,500 A | * | 6/1977 | Fletcher et al. | 75/135 |
| 4,048,063 A | * | 9/1977 | Cheng | 210/72 |
| 4,151,215 A | | 4/1979 | Phillips | |
| 4,153,546 A | * | 5/1979 | Hammel et al. | 210/41 |
| 5,158,690 A | * | 10/1992 | Batchelder et al. | 210/775 |

FOREIGN PATENT DOCUMENTS

| | | |
|---|---|---|
| EP | 0 349 117 | 7/1993 |
| WO | WO97/14033 | 4/1997 |

OTHER PUBLICATIONS

G.S. McNab et al., "Thermophoresis in Liquids", Journal of Colloid & Interface Science, vol. 44, No. 2, Aug. 1973, pp. 339–346.*

A.F. Andreev, "Thermophoresis in Liquids", Sov. Phys. JETP, vol. 67, No. 1, Jan. 1988, pp. 117–120.*

PCT Notification of Transmittal of the International Search Report, issued Oct. 17, 2000.

S. Weinstein, Ph.D. et al, Detection of Extremely Low Concentration of Ultra Pure TNT By Rat, in Proc. 3rd Int. Symp. on Analysis and Detection of Explosives, Manheim-–Neuostheim, Germany, pp. 32.1–32.4, 1989.

Pavel Neudorfl et al., Research Programme on Explosives Vapour Detection at NRC, Journal of Energetic Materials vol. 4, pp. 415–445. 1986, Bowden, Brodman & Devine, Inc.

W. McGann et al., A Thermodynamic Study of the Vapor Pressures of C–4 and Pure RDX, presented at the 1st Int. Symp. Explosives Vapor Detection Technol., Atlantic City, NJ, 1991, pp. 518–531, 1991.

(List continued on next page.)

Primary Examiner—Jill Warden
Assistant Examiner—Monique T. Cole
(74) Attorney, Agent, or Firm—Cesari and McKenna, LLP (57) ABSTRACT

The method and apparatus of the invention create a dynamic Soret effect for propelling a target chemical constituent along a pathway. A moving temperature profile impressed upon the pathway produces consecutive alternating warmer and cooler zones along the path which transport components of a mixture down the path according to their respective diffusivities. In one embodiment, the invention provides a dynamic thermophoretic concentrator for separating a target chemical constituent from a mixture of components on the basis of diffusion coefficient by using alternate forward and backward motion of a temperature profile along the pathway, thereby accumulating an ultimate concentration of the target constituent greater than its initial concentration in the mixture.

26 Claims, 6 Drawing Sheets

OTHER PUBLICATIONS

E.M. Boncyk, A Bioluminescent Explosives Vapor Detection and Identification System, in Proc. 3rd Int. Symp. on Analysis and Detection of Explosives, Mannheim–Neuostheim, Germany, pp. 40.1–40.14, 1989.

PH.H. Abelson et al., Separation of Uranium Isotopes by Liquid Thermal Diffusion, Proceedings of the Symposium on Isotope Separation, Amsterdam, 1957. pp 483–508.

Sydney Chapman et al., The Mathematical Theory of Non-Uniform Gases; An Account of the Kinetic Theory of Viscosity, Thermal Conduction, and Diffusion in Gases, 1958 Chapter 14, pp. 244–258. Cambridge at the University Press.

L. Waldmann et al., Thermophoresis and Diffusiophoresis of Aerosols, Aerosol Science, ed.C.N. Davies, Academic Press, New York, 1966. pp. 137–162.

W.C. Hinds, Thermal and Other Radiometric Forces, Aerosol Technology, Wiley and Sons, New York, 1982, Ch. 8, pp. 153–163.

G.H. Geiger et al., Transport Phenomena in Metallurgy, pp. 59–67, Addison–Wesley Publishing Company, Reading, Massachusetts, 1981.

S. Chapman et al., A Note on Thermal Diffusion, pp 248–253. Phil. Mag. 33, 1917.

Von D. Enskog, Comments on a Fundamental Equation in the Theory of Kinetic Gasses, Phys, Z. 12 (56), 533, 1911.

Ho–Ming Yeh et al., Separation Theory in Thermal Diffusion Columns, Handbook of Heat and Mass Transfer, Gulf Publishing Company Book Division, 1986, vol. 2 chp. 35, pp. 1411–1427.

John S. Suehle et al., Tin Oxide Gas Sensor Fabricated Using CMOS Micro–Hotplates and In–Situ Processing, IEEE Electron Device Letters vol. 14, No. 3, 118–120, 1993.

R.E. Cavicchi et al., Fast Temperature Programmed Sensing for Micro–Hotplate Gas Sensors, IEEE Electron Device Letters vol. 16, 286–288, 1995.

* cited by examiner

THERMOPHORETIC PUMP AND CONCENTRATOR

This invention was made with government support under contract number F19628-95-C-0002 awarded by the Air Force. The government has certain rights in this invention.

BACKGROUND OF THE INVENTION

Detection of trace amounts of illicit substances such as explosives and narcotics is an ever more critical element of combating terrorism and contraband. However, the exacting operating requirements a detector must meet in order to be useful for these purposes severely limit the number of suitable technologies.

The primary operating requirement is sensitivity. Many of the materials targeted by law enforcement or security screenings are present in the gas phase at very low fractional molecular concentrations. Table 1 shows approximate values of room-temperature vapor pressures for common explosives and cocaine, reports of which often vary by as much as an order of magnitude.

TABLE 1

| explosive | vapor pressure in air at room temperature (atm) |
| --- | --- |
| glycerol trinitrate ("NG") | $10^{-7}$ |
| 2,4,6 trinitrotoluene ("TNT") | $10^{-8}$ |
| 1,3,5-trinitro-1,3,5-triazacyclohexane ("RDX") | $10^{-12}$ |
| pentaerythritol tetranitrate ("PETN") | $4 \times 10^{-13}$ |
| C-4 (due to plasticizer and RDX) | $10^{-14}$ |
| cocaine | $10^{-10}$ |

Realistic use in demanding security environments, entailing screening thousands of containers per day, would further require that each determination be completed rapidly, in well under a second. For many law enforcement situations, a serviceable illicit substance detector would necessarily be portable.

Many sensing devices have been proposed for detecting trace amounts of explosives or drugs in security or law enforcement contexts. However, none has combined the sensitivity to detect constituents present at concentrations as low as $10^{-12}$ atm with the requisite rapidity and portability.

For example, a bioluminescence-based explosives detection and identification system capable of detecting constituents in air having a fractional molecular concentration on the order of $10^{-14}$ has been proposed. However, the required processing time is on the order of several minutes. (See, e g, E. M. Boncyk in *Proc. 3rd Int. Symp. on Analysis and Detection of Explosives*, Mannheim-Neuostheim, Germany, 4.1–40.14 [1989].)

Ion mobility spectrometry ("IMS") has found wide application as a relatively quick and accurate technology for detecting explosives and illicit drugs. The nominal sensitivity of IMS-based systems ranges from about $10^{-12}$ to $10^{-14}$ atm. As is typical of gas-phase sensors, the minimum level of a target compound detectable by this technique is limited by false positives and interference from other gaseous constituents rather than by the inherent capability of the sensor.

The reliance of standard IMS on the ion charge-to-mass ratio to differentiate constituents predisposes it to false positives when used to detect explosives or drugs. For example, the ion mobility spectrum obtained from methamphetamine, a product of cocaine decomposition, overlaps on the time axis with that due to a common skin conditioner ingredient, so that this ingredient provokes a false positive by an ion mobility spectrometer configured to detect methamphetamine. Introducing an ionizable vapor dopant that neutralizes the problematic skin conditioner ingredient but not molecules of explosives or methamphetamine—which have exceptionally large electron or proton affinities—mitigates this difficulty, but at the expense of some increase in system complexity. Impurities remaining in the sensor from a previous screening are another significant source of error in IMS-based systems.

Also, substances such as RDX and PETN having vapor pressures near the lower limits of detectability by IMS can be detected by this method only after several seconds of sampling. Such an interval is unacceptably long for high-volume applications, such as comprehensive passenger screening at airports.

BRIEF DESCRIPTION OF THE INVENTION

Objects of the Invention

It is, accordingly, an object of the present invention to provide method and apparatus for enhancing the capability of detectors with respect to trace constituents.

It is another object of the present invention to provide method and apparatus or eliminating interfering background impurities prior to subsequent downstream detection.

It is another object of the invention to provide method and apparatus for rapidly detecting trace constituents.

It is another object of the invention to reduce the occurrence of false positives in ion mobility spectrometry systems.

It is another object of the invention to provide method and apparatus that allow easy and quick clearing of a sensor system.

It is yet another object of the invention to provide suitable method and apparatus for detecting illicit drugs and explosives and decomposition products thereof in law enforcement and security environments.

SUMMARY OF THE INVENTION

The invention provides method and apparatus for propelling a target chemical constituent, or equivalently a set of constituents, along a pathway by applying a time-varying temperature profile along the pathway so as to effect a dynamic Soret effect. The temperature profile impressed upon the pathway creates at least one region over which temperature varies with position, so as to produce a warmer zone and a cooler zone situated consecutively along the path. In accordance with the Soret effect, components present at dilute concentration in a carrier medium segregate in the temperature gradient according to their respective molecular weights. Components having molecular weights greater than that of the carrier medium accumulate in the cooler zone, whereas components having higher molecular weights diffuse toward the warmer zone. In moving to establish this thermally driven concentration gradient, each component advances toward the appropriate portion of the temperature profile at a respective net average velocity known to those of skill in the art as its Soret velocity.

In accordance with the invention, the region of temperature variation is displaced along the pathway at a wave velocity, so as to generate a time-varying temperature profile. As the local temperature changes, the segregated dilute components move so as to preserve or reestablish the thermally induced concentration gradient. Thus the components are conveyed along the pathway with the moving region of temperature variation. The quantity of a particular constituent that is pumped down the path depends on the temperature gradient, the absolute value of the wave velocity and its relative value compared to the constituent's Soret velocity, and also the diffusion coefficient of the constituent in the carrier medium.

In one embodiment, the invention provides a dynamic thermophoretic concentrator for separating a target chemical constituent from a mixture of components on the basis of diffusion coefficient by using alternate forward and backward motion of the temperature profile along the pathway, thereby accumulating an ultimate concentration of the target constituent greater than its initial concentration in the mixture by a factor up to ten, 100, $10^3$, $10^4$ or even greater. Because most components have very similar Soret velocities, as a practical matter the distribution of a constituent across a given moving temperature profile depends mainly on its diffusion coefficient. Particles having small diffusion coefficients, correlating with large particle sizes, are concentrated in the cooler portion of the temperature profile more compactly, and thus transported at a greater flux by the time-varying profile; the degree of localization drops rather abruptly with increasing diffusion coefficient, so that smaller constituents are distributed more evenly throughout the region of varying temperature and less efficiently transported. The diffusion coefficient at which the flux declines can be shifted to higher values by increasing the temperature difference between the warmer and cooler extremes. For a given temperature gradient, the basic shape of the flux-diffusivity function changes with the wave velocity.

In accordance with the invention, the temperature profiles and wave velocities used for forward and backward motion are chosen in conjunction to enhance the net forward flux of a target constituent, and suppress that of other constituents, based on diffusivities, thereby preferentially conveying the target constituent forward. For example, distinct forward and backward thermal profiles, differing from one another in shape or temperature gradient, may be used. Or, in a preferred embodiment, a single temperature profile is moved at different forward and backward wave velocities. In particular, a target constituent is concentrated at an end of the pathway by alternately moving the temperature profile toward the end at a forward wave velocity greater than the constituent's Soret velocity and away from the end at a backward wave velocity less than the constituent's Soret velocity.

The invention is compatible with micrometer-scale implementation, allowing for a reduction in both concentration time and power requirement compared to concentrators known in the art. Its speed and portability suit it for security and law enforcement applications and its sensitivity is equal to detecting residues of explosives and narcotics or their decomposition products. To this end, the thermophoretic concentrator of the invention is particularly advantageous when used in conjunction with a fluid phase detector, for example an ion-mobility spectrometer. The use of diffusivity as a discriminator enables ion-mass spectrographic systems to differentiate between a target constituent and other, confounding dilute components, thereby abating false positive indications.

The ability to selectively preconcentrate an arbitrary dilute constituent by several orders of magnitude and also to eliminate background impurities before subsequent downstream detection mitigates the limitation on minimum detectable constituent level inherent to most gas-phase sensors. Furthermore, by wholesale backward pumping the dynamic thermophoretic concentrator of the invention is able to clear the system of extraneous impurities between uses in less time than is required to detect a target constituent.

BRIEF DESCRIPTION OF THE DRAWINGS

The invention description below refers to the accompanying drawings, not necessarily to scale, of which:

FIGS. 3A through 3C schematically depicts constituent concentration in the cooler zone of a thermal profile including a region over which temperature is a nonconstant function of position, wherein FIG. 3A illustrates a stationary or relatively slowly-moving profile, and FIGS. 3B and 3C illustrate more rapidly moving profiles;

DETAILED DESCRIPTION OF AN ILLUSTRATIVE EMBODIMENT

When a thermal gradient is impressed on a gas mixture in a closed container, the components thermophoretically diffuse until an equilibrium concentration is reached. The partial pressure ratio of a constituent i $$R_i = \frac{X_{iLow}}{X_{iHigh}},$$

in which $X_{High}$ and $X_{Low}$ are the ratios of the constituent's partial pressure to the total pressure in the higher and lower temperature regions, respectively. $R_i$ depends on the high and low temperatures in the container, $T_{High}$ and $T_{Low}$, and the thermophoresis coefficient $\alpha_{ij}$ for the constituent i in carrier medium j as follows:

$$R_i = \frac{X_{iLow}}{X_{iHigh}} = \left[\frac{T_{Low}}{T_{High}}\right]^{\alpha_{ij}}.$$

Figure 1:
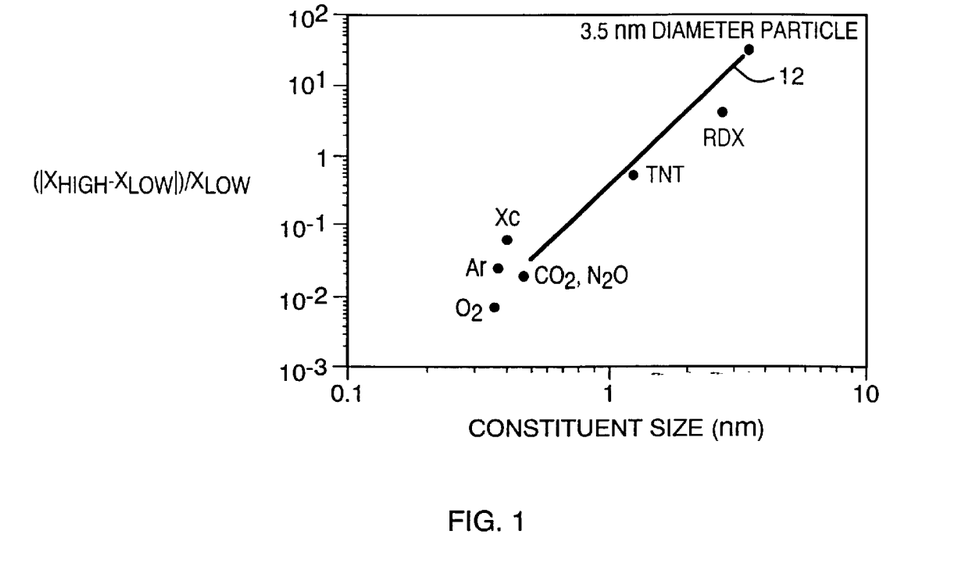
FIG. 1 graphically depicts the concentration enhancement of dilute constituents in gaseous nitrogen between a cooler region at $T_{Low}=100°$ C. and a warmer region at $T_{High}=300°$ C.

For example, a temperature difference of a few hundred degrees centigrade in a carrier gas of nitrogen can cause higher molecular weight gases to increase their partial pressures by more than 100% in the lower temperature region. FIG. 1 shows the normalized absolute concentration increase for several dilute constituents in gaseous nitrogen between a cooler zone at $T_{Low}=100°$ C. and a warmer zone at $T_{High}=300°$ C. The solid line 12 is calculated for constituents having molecular weights greater than 40 atomic mass units. (The thermophoretic data presented herein for TNT and RDX is estimated from their molecule sizes and from published data for both smaller and larger components in nitrogen.)

Figure 2:
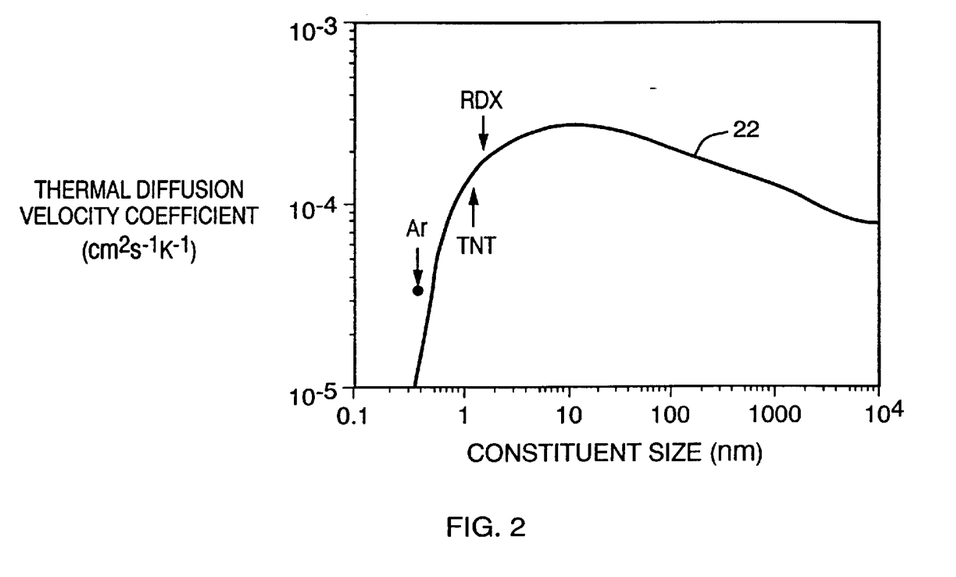
FIG. 2 shows the approximate dependence of thermal diffusion velocity coefficient on constituent particle size in gaseous nitrogen.

Molecules of each constituent i undergoing thermally driven diffusion move at a respective average thermal drift velocity $$V_{iSoret} = \Theta_i \frac{dT}{dx} = \frac{D_{ij}\alpha_{ij}}{T}\frac{dT}{dx},$$

in which $\Theta_i$ is the constituent s thermal diffusion velocity coefficient, $D_{ij}$ is its diffusion coefficient in the carrier gas, T is the local temperature, and $$\frac{dT}{dx}$$

is the local thermal gradient. In FIG. 2, curve 22 approximately shows the dependence of thermal diffusion velocity coefficient on dilute constituent particle size in gaseous nitrogen. For particles having diameters from about 1 nanometer to about 1 micrometer in diameter, variations in diffusion and thermophoresis coefficients are roughly compensatory so that constituents in this range have nearly the same value of $\Theta$, on the order of $2.4\times10^{-4}$ cm$^2$s$^{-1}$K$^{-1}$. (For smaller constituents, the force generated by the thermal gradient does not scale as neatly with size but rather depend on details of the intermolecular interactions and approaches zero as the size and molecular weight of the dilute constituent approach that of the carrier gas.) However, the magnitude of $V_{Soret}$ for species in this size range can be adjusted by choice of the thermal gradient.

Figure 3A:
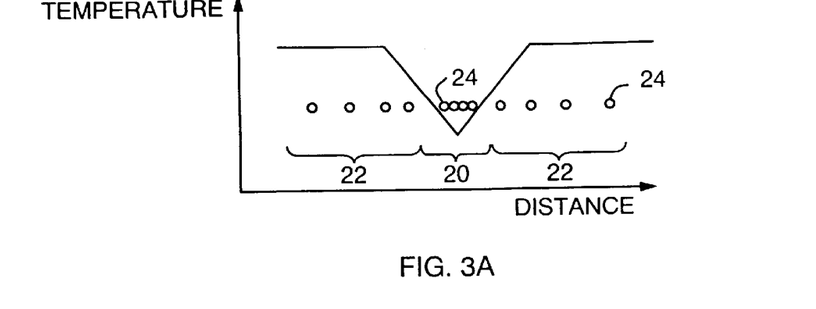
Figure 3B:
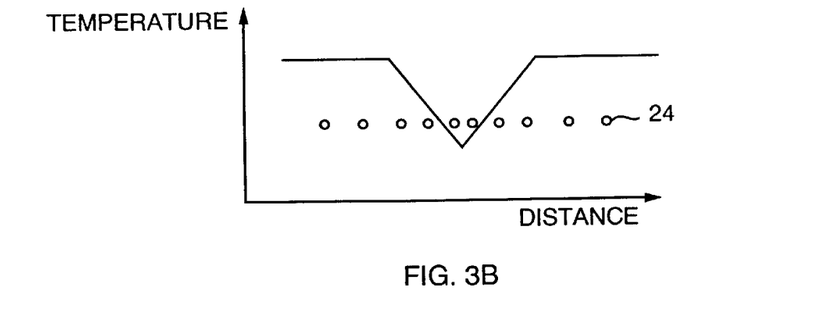
Figure 3C:
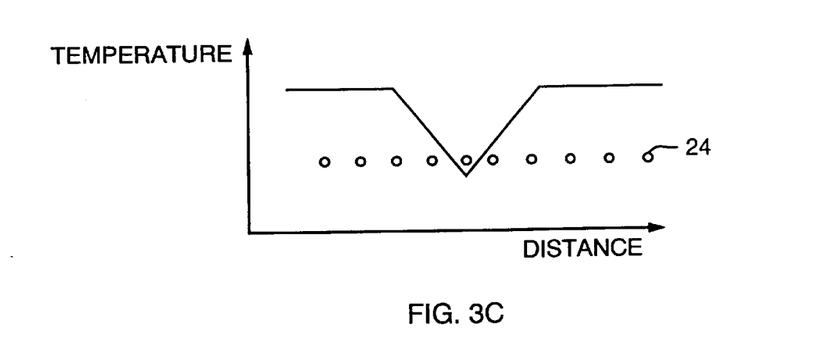
Figure 7:
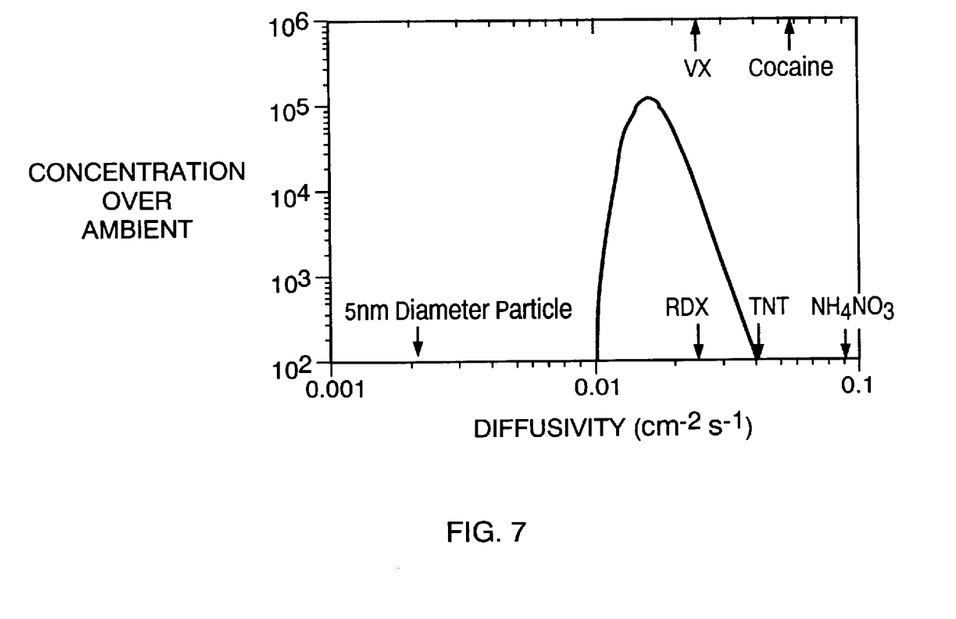
FIG. 7 graphically depicts the calculated concentration of constituents resulting from bidirectional pumping as a function of diffusivity.

FIG. 3A shows a thermal profile including a region over which temperature is a nonconstant function of position so as to encompass a cooler zone 20 and a warmer zone 22 along an axis defining a pathway. Molecules of a dilute constituent having a greater molecular weight than that of the carrier gas collect preferentially in the cooler zone 20, as represented by circles 24. If, in accordance with the invention, the region of nonconstant temperature is displaced along the pathway at a thermal wave velocity $V_{wave}$ the local constituent distribution adjusts so as to maintain the thermally induced concentration gradient as the local temperature changes. If the thermal wave velocity is less than the Soret velocity, the thermally induced drift is sufficiently rapid to follow the temperature profile motion, so that the aggregation of the constituent in the cooler zone 20 is preserved as depicted in FIG. 3A. Under these conditions, the moving cooler zone is able to efficiently transport dilute constituent. As $V_{wave}$ increases, the degree of constituent confinement in the cooler zone diminishes, as depicted in FIG. 3B, in which the wave and Soret velocities are comparable, and FIG. 3C, for which the wave velocity is greater than the Soret velocity. As $V_{wave}$ surpasses $V_{Soret}$ the constituent distribution approaches uniformity along the pathway. Transport of dilute constituent by the cooler zone 20 becomes less efficient.

Since most components have similar Soret velocities, for a given thermal wave velocity, the extent to which one dilute constituent is confined to the moving cooler zone, compared to another constituent, is largely determined by the relative values of the constituents' diffusivities. Large particles greater than 2 nanometers in diameter, generally having values of $D_y$ less than 0.01 $cm^2s^{-1}$, have comparatively large values of $\alpha_y$, and are relatively easily concentrated in-the cooler zone. The intermediate diffusivities of, for example RDX, TNT and cocaine, on the order of 0.04 $cm^2s^{-1}$, afford somewhat less concentration. Small particles, such as common air components oxygen, carbon dioxide, argon and xenon, have diffusivities greater than 0.1 $cm^2s^{-1}$ and tend to scatter more uniformly along the path.

FIG. 4 shows a symmetrical sawtooth temperature profile comprising a series of alternating cooler 20 and warmer 22 zones and along the pathway. For a dilute constituent having a given diffusivity, the effect that displacing such a series of zones along the path has on the constituent distribution along the pathway is determined by the temperature difference ΔT of the sawtooth profile and by the thermal wave velocity. In accordance with the invention, adjusting these operating parameters tailors the composition of the fluid selected from the component mixture and moved by the time-varying temperature profile, on the basis of constituents' diffusivities.

With reference to FIG. 5, the modeled normalized flux as a function of constituent diffusivity is illustrated by curve 40 for a sawtooth profile with ΔT=50° C. moving at $V_{wave}$=0.1 $V_{Soret}$, assuming that the components of the fluid mixture do not adhere to the surfaces defining the pathway. The flux declines as $D_y$ exceeds about $5\times10^{-4} cm^2s^{-1}$. In comparison, the knee of curve 42, corresponding to ΔT=200° C., is shifted to higher diffusivity values. The declivity of curve 44, for which ΔT=200° C. and $V_{wave}$=3 $V_{Soret}$, is more shallow, so that the relative flux of the higher-diffusivity constituents, compared to that of the lower-diffusivity components, is enhanced. In this case, the smaller quantity of constituent carried in each cooler zone 20 at high wave velocities is offset by the much greater number of zones traversing the path per unit time; even constituents very poorly contained in a zone are transported in some quantity. (Please note that for illustration purposes, the low-diffusivity plateaus of the flux curves 40, 42 and 44 are all normalized to a common value. In fact, as diffusivity approaches zero, so that perfect confinement is achieved, the faster-moving profile must produce a greater flux than does the slower one.)

In a preferred embodiment, the invention incorporates displacement of the region of nonconstant temperature alternately in opposite directions, thereby concentrating a target constituent. FIG. 6 demonstrates the use of such bidirectional thermophoretic pumping to concentrate from a dilute gaseous solution only those constituents belonging to a selected portion of the diffusivity spectrum. Corresponding to a profile with ΔT=200° C. and $V_{wave}$=3 $V_{Soret}$ as depicted by curve 42, curve 62 represents the diffusivity profile of the fluid components transported by a forward-moving sawtooth. Curve 64 corresponds to curve 44 and represents the same pattern and gradient moving backward at $V_{wave}$=0.1 $V_{Soret}$. The difference between these, curve 66, shows the net effective movement of constituents along the path as a function of diffusivity. The fast forward pumping efficiently moves low- and intermediate-diffusivity constituents by virtue of the large number of cooler zones advancing per unit time. The slower backward pumping culls the constituents that are too large to be of interest but were conveyed forward during the fast phase.

If the end of the pathway is blocked, the concentration of a constituent for which the net flux is positive increases at the blocked end until its back diffusion comes into equilibrium with its forward net pumping flux. FIG. 7 shows the calculated resulting concentration of dilute constituents in nitrogen as a function of constituent diffusivity. Constituents with values of diffusivity greater than that of RDX are not concentrated to any significant degree while those with smaller values are reverse-pumped to the rear of the pathway. By changing $\Delta T$ or $V_{wave}$, other preselected constituents could be concentrated.

Figure 8:
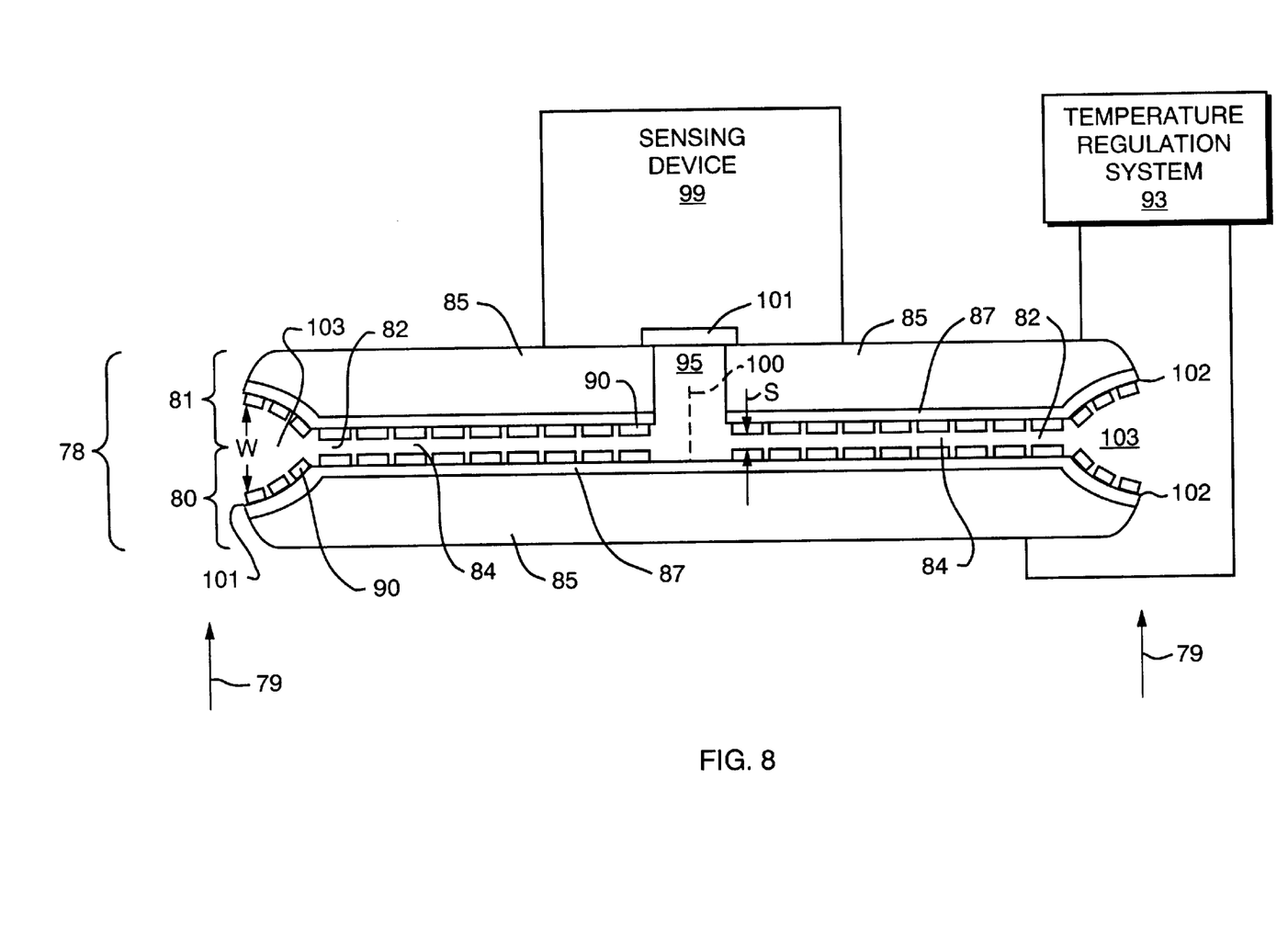
FIG. 8 shows, in cross-section, an apparatus for pumping a chemical constituent along a pathway.

FIG. 8 shows, in cross-section, an apparatus 78 for pumping a chemical constituent from a fluid flowing in the direction indicated by arrows 79, as prescribed by the invention. A disk 80 opposes a parallel annulus 81 to form a radial pathway 82 therebetween, including a first end at the circumferential edges 102 and second end near the centers 100 of the disk 80 and annulus 81. The pathway 82 includes a passage 84 and an inlet area 103. The disk 80 and annulus 81 each comprise a substrate 85 and a thermally insulating layer 87, facing the pathway 82, over which is patterned a resistive material 90 forming distinct rings on the disk 80 and annulus 81, concentric around the center of the annulus 81. A temperature regulation system 93, such as is well known to those of skill in the art, is coupled to the resistive material 90 for controlling the respective temperature of each ring so as to generate a moving thermal profile. (Optionally only one of the disk 80 and the annulus 81 bears the resistive material 90.) A circular channel 95 through the center of the annulus 81 optionally communicates with a sensing device 99 for analyzing the fluid composition delivered to the center 100 of the annulus by the pumping apparatus 78. The apparatus 78 may include a barrier 101 covering the channel 95 so as to allow a target constituent to accumulate near the channel 95 and operated so as to periodically open and admit components in the channel 95 into the sensing device 99. Other separated member configurations, such as those including rectangular plates or members of other shapes, with other pathway orientations, for example from one edge of a member to its opposite edge, are also compatible with the invention.

Figure 4:
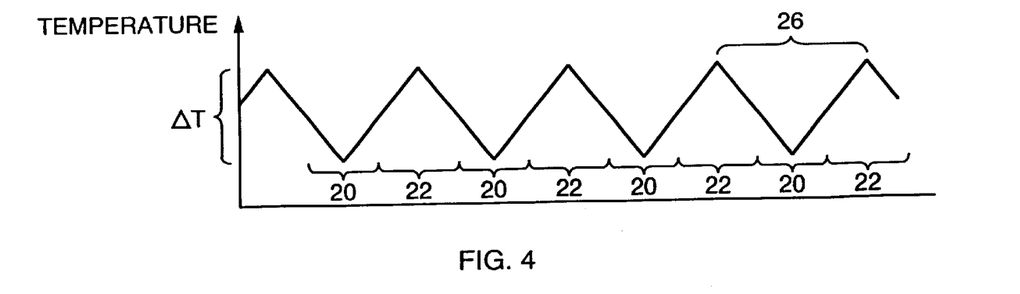
FIG. 4 shows a thermal profile having a series of alternating cooler and warmer zones along the pathway.
Figure 5:
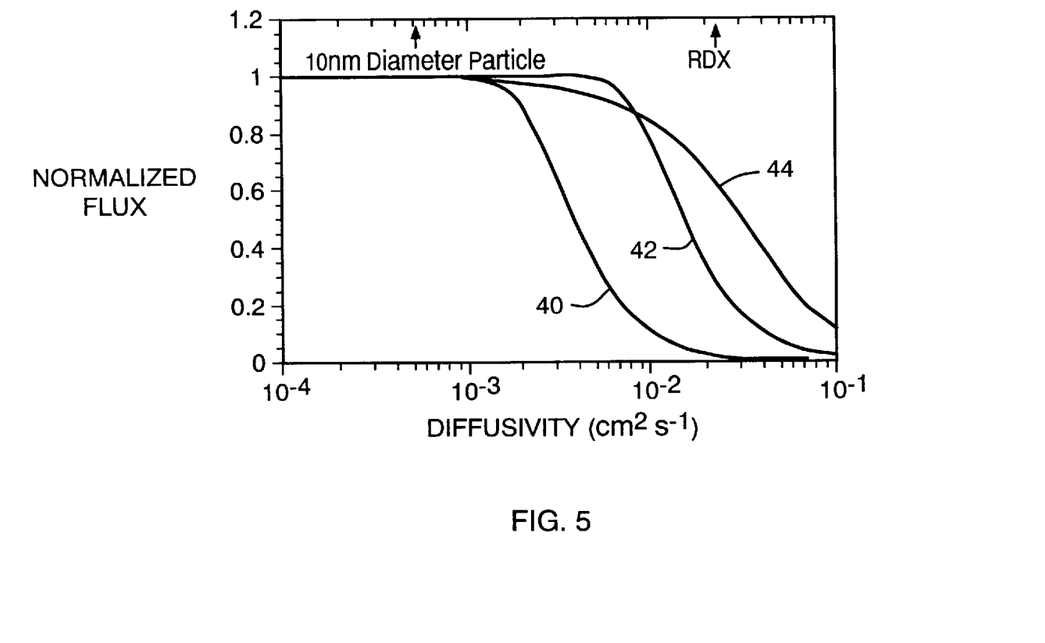
FIG. 5 graphically depicts the modeled normalized flux carried by moving thermal profiles as a function of constituent diffusivity.
Figure 6:
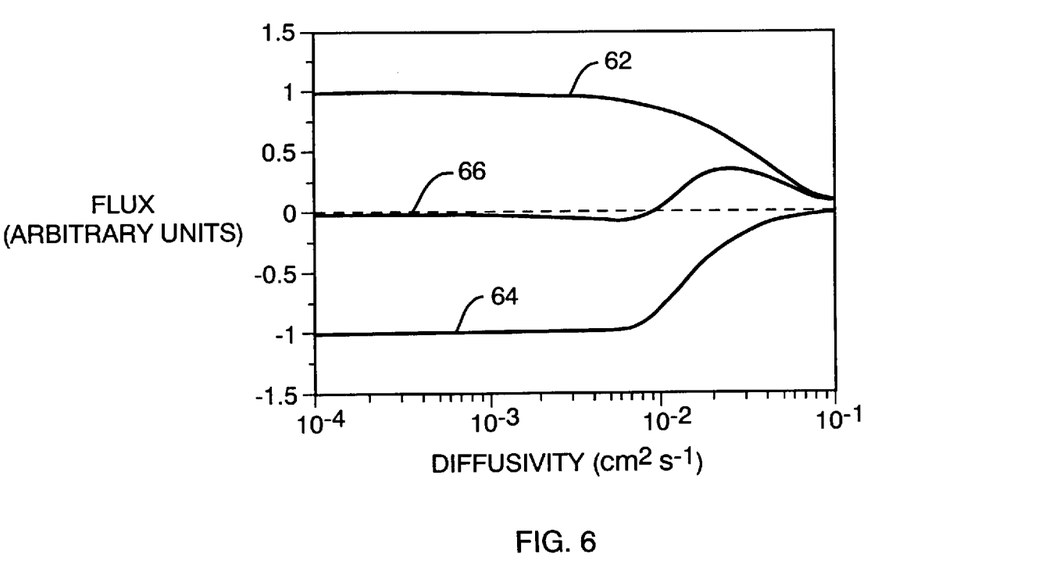
FIG. 6 graphically depicts the net normalized flux carried by a bidirectionally moving thermal profile as a function of constituent diffusivity.

An annulus 81 having a diameter of 2 cm with a channel diameter of 1 mm can accommodate 950 concentric resistively heated rings each measuring 10 $\mu$m along the radius. (Such micrometer-sized heating elements are known to those skilled in the art. See, for example, J. S. Suehle et al, in *IEEE Electron Device Letters* 14, 188–120 [1993] and R. E, Cavicchi et al. ibid 16, 286–288 [1995]). Using six rings to create each tooth 26 of the thermal profile shown in FIG. 4 would be appropriate for a spacing s of about 20 $\mu$m between the disk 80 and the annulus 81; the length of the sawtooth 24 is preferably much larger than the spacing s in order to minimize smearing of the thermal gradients in the direction perpendicular to the surface of the resistive material 90. Assuming that air passes over the edges 102 of the apparatus 78 at 600 cm$^{-1}$, this configuration would be able to concentrate a selected constituent by a factor as large as 10$^5$, as shown in FIG. 7, in several tens of seconds. The concentrating power of the apparatus 78 grows exponentially with the number of teeth 24 used along the passage 84. The small thermal time constants, less than 0.1 millisecond, of the heating elements enable quick accumulation of a threshold concentration at the second end of the pathway, near the centers 100 of the disk 80 and annulus 81. Larger resistive elements, such as those measuring up to 20 $\mu$m, 50 $\mu$m, or 100 $\mu$m along the pathway are also compatible with the apparatus of the invention.

Figure 9:
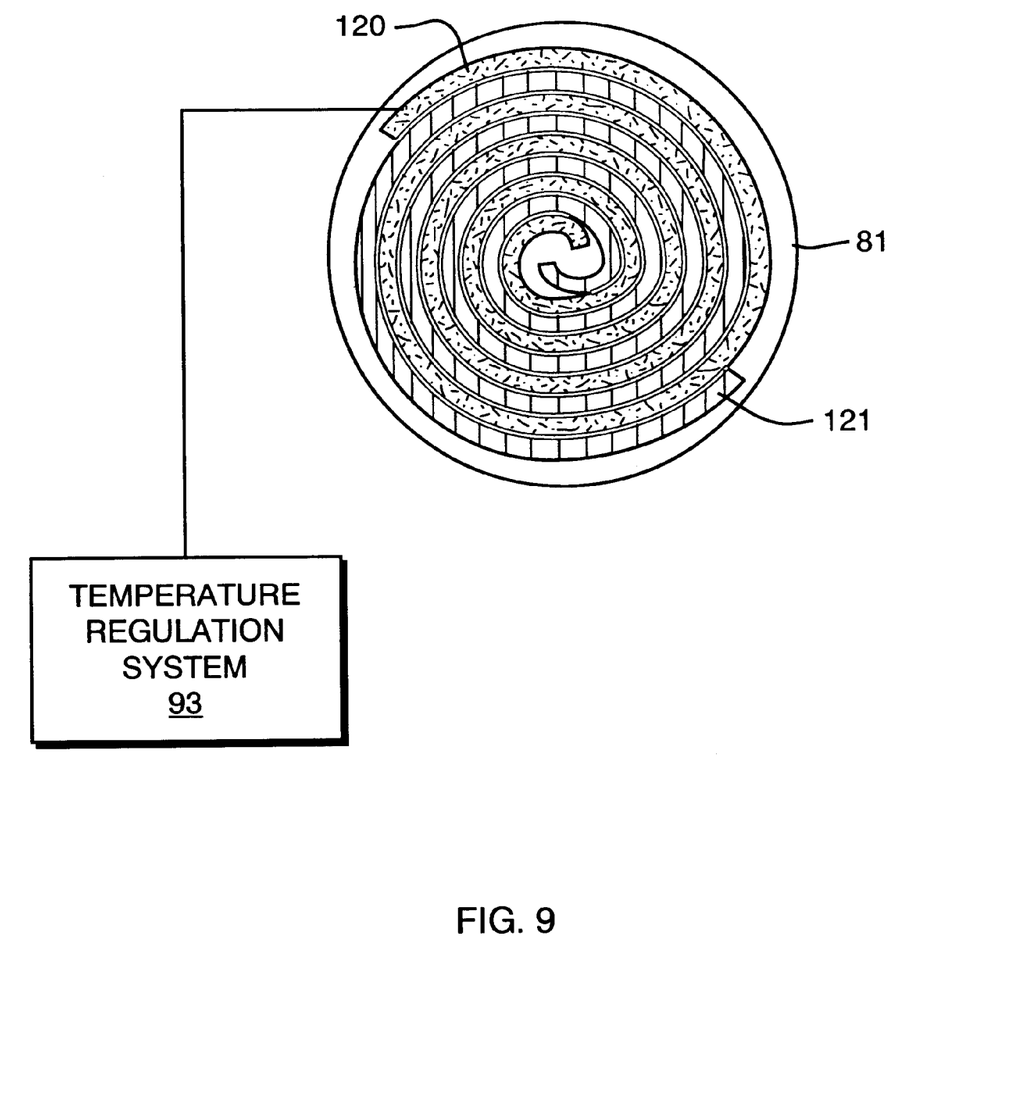
FIG. 9 shows an annular member bearing two interspersed serpentine heating elements.

In an alternate embodiment, the resistive material 90 is arranged on the disk 80 and/or the annulus 81 in continuous spiral or serpentine elements. Such a configuration of two spiral elements 120 and 121 is shown in FIG. 9. The use of two or several interspersed serpentine elements simplifies the operation of the temperature regulation system 93 by reducing, compared to a concentric ring configuration, the number of elements that must be individually addressed in forming the moving thermal profile.

The features and movement of the thermal gradient in the passage 84 are constructed by the temperature regulation system 93 to selectively deliver a target constituent or set of constituents to the center 100 of the annulus 81. In operation, the extreme temperatures of the moving thermal profile are chosen to be sufficiently high so as to inhibit adherence of the atmospheric components on the interior surfaces of the disk and the annulus but sufficiently low to prevent thermal decomposition of the target constituent.

In order to minimize power consumption, it is desirable that the substrate portion 85 of the disk 80 and annulus 81 have an adjustable thermal conductivity, for example by comprising a cavity (not shown) facing the insulating layer 87 with a variably conductive medium such as air filling the cavity. An alternative is a solid substrate of a moderately conductive material such as silicon.

The temperature regulation system 93 of an embodiment incorporating a 100-nm-thick thermally insulating layer 87 of silicon dioxide or silicon nitride patterned with 50-nm-thick resistive elements 90 of polysilicon, tantalum or chromium would supply approximately 25 W of heater power and extract power at the same rate. The modeled operating power is linearly dependent on the time required for constituent concentration. For example, if reaching the desired concentration in 0.1 second requires 25 W, then only 2.5 W is needed to achieve the same concentration in 1 s. If a lower ultimate concentration can be tolerated, fewer zones are needed along the pathway, and the power requirement is decreased. For example, if the ultimate concentration factor is only 10, then only 5 W is required. The actual power requirements may also depends on other variables such as the algorithm used to switch the power to the resistive heaters 90.

Typically, the ability to detect a target constituent within a particular time interval depends more upon the ability of the sensing device 99 to collect a minimum detectable absolute amount of the target constituent than its ability to concentrate the constituent by several orders of magnitude. Thus is preferable to sample a large volume of fluid in order to detect a constituent quickly. A large separation between the disk 80 and annulus 81 would facilitate sampling of the fluid flowing in the direction of arrow 79 across the edge 101 of the apparatus 78. However, smaller separations would allow larger thermal gradients to be generated, supporting more selective pumping of the target constituent.

A spacing s of about 20 $\mu$m between the interior surfaces of the disk 80 and the annulus 81 allows the resistive elements to generate sufficient thermal gradients to effectively separate constituents from the fluid mixture. Preferably, the spacing s increases near the exterior edges 102 to form a relatively wide inlet area 103 to facilitate sampling a large volume of air in order to detect a target constituent quickly. A suitable inlet area 103 would have a depth along the diameter of about 1 mm and a width w on the order of 100 $\mu$m, giving a two-centimeter device a sampling area of 6 mm$^2$. As fluid flows across the edge 102, a boundary layer forms, out of which the components of the fluid diffuse into the inlet area and are pumped wholesale by the moving thermal profile into the narrower passage 84. In congruity with the larger spacing w, broader teeth 24, on the order often or twenty times longer than those in the passage 84, are used, so generating smaller temperature gradients for the same extreme temperatures. Also, since the purpose of the time-varying profile in the inlet area 103 is to deliver components of the fluid without discrimination, to improve sampling by the passage 84, this thermal profile is moved only away from the edges 102 and only at a relatively slow wave velocity, less than the Soret velocity.

When the apparatus 79 is operated to selectively preconcentrate a target constituent for transport down the passage 84, it may be desirable to couple the end of the pathway at the center 100 of the annulus 81 to a sensor device 99. In general, the sensor device 99 detects and determines the concentration of the target constituent delivered by the preconcentrator. Many types of sensor devices suitable for use in conjunction with the preconcentrator of the invention are known to those skilled in the art. The ion mobility spectrometer ("IMS"), is one such sensor device. In this case, a constituent laser ionizer for photoionizing the components concentrated near the channel 95 may be adjoined to the apparatus 79 through an aperture, not shown, in the disk 80.

The ability of the thermophoretic apparatus to increase the concentration of the target constituent as well as to eliminate other interfering impurities, substantially increases the sensitivity of the resultant system over the sensor device alone. Also, the ability of the thermophoretic concentrator apparatus 79 of the invention to differentiate between components of a fluid mixture on the basis of diffusivity adds a new dimension to the detection and characterization abilities of IMS-based systems because it eliminates confusion between components having overlapping spectra.

The thermophoretic concentrator of the invention has the ability to actively pump constituents out of the pathway 82 as well as pumping them toward the detector, making it possible to clear the system of gaseous impurities in less time than that required to detect a target constituent. Particle contamination can be burned or blown out by quickly increasing the temperature of the concentrator to several hundred degrees.

It will therefore be seen that the foregoing represents a highly advantageous approach to collecting and sorting target constituents from a mixture in a carrier medium, especially for enhancing the detector sensitivity and selectivity of detecting very dilute constituents. The terms and expressions employed herein are used as terms of description and not of limitation, and there is no intention, in the use of such terms and expressions, of excluding any equivalents of the features shown and described or portions thereof, but it is recognized that various modifications are possible within the scope of the invention claimed. For example, the moving thermal profiles need not be symmetrical or sawtoothed in form; or rather than a gas, the medium from which the target constituent is sorted may be a liquid, a gel, or a solid—for example silicon dioxide through which alkali metals diffuse. In such embodiments, the pathway may be defined within the fixed boundaries of the condensed phase. Furthermore, the pathway may be defined by a tube rather than by opposite members; the moving thermal profile may generated by moving wires or other elements instead of integral resistive elements.

What is claimed is:

1. A method of concentrating a target chemical constituent having a Soret velocity from a mixture of components, the method comprising the following steps:
   providing a pathway over which components are free to move, the pathway having first and second ends;
   controlling temperature so as to create consecutive warmer and cooler zones, along the pathway;
   supplying the mixture of components to the pathway; and
   moving the zones together along the pathway
      toward the second end at a forward wave velocity, and then
      toward the first end at a backward wave velocity,
   whereby the target constituent collects in a cooler zone more than to in a warmer zone so that the major portion of the target constituent is conveyed to the second end.

2. The method of claim 1 wherein the forward wave velocity is greater than the Soret velocity and the backward wave velocity is less than the Soret velocity.

3. A method of concentrating a target chemical constituent from a mixture of components, the method comprising the following steps:
   providing a pathway over which components are free to move, the pathway having first and second ends;
   controlling temperature so as to create consecutive warmer and cooler zones along the pathway;
   supplying the mixture of components to the pathway; and
   moving the zones together along the pathway
      toward the second end at a forward wave velocity, and then
      toward the first end at a backward wave velocity, wherein moving the zones toward the second end transports the target constituent and moving the zones toward the first end transports at least one component larger than the target constituent preferentially at a greater rate than the target constituent, so that the major portion of the target constituent is conveyed to the second end.

4. A method of concentrating a target chemical constituent from a mixture of components, the method comprising the following steps:
   providing a pathway over which components are free to move, the pathway having first and second ends;
   controlling temperature so as to create consecutive warmer and cooler zones along the pathway;
   supplying the mixture of components to the pathway; and
   moving the zones together along the pathway
      toward the second end at a forward wave velocity, and then
      toward the first end at a backward wave velocity, said forward wave velocity being unequal to the backward wave velocity, so that the major portion of the target chemical constituent is conveyed to the second end.

5. A method of concentrating a target chemical constituent from a gaseous mixture of components, the method comprising the following steps:
   providing a pathway over which components are free to move, the pathway having first and second ends;
   controlling temperature so as to create consecutive warmer and cooler zones along the pathway;
   supplying the mixture of components to the pathway; and
   moving the zones together along the pathway
      toward the second end at a forward wave velocity, and then
      toward the first end at a backward wave velocity, so that the major portion of the target chemical constituent is conveyed to the second end.

6. A method of concentrating a target chemical constituent from a mixture of components said mixture constituting a gel, the method comprising the following steps:
   providing a pathway over which components are free to move, the pathway having first and second ends;

controlling temperature so as to create consecutive warmer and cooler zones along the pathway;

supplying the mixture of components to the pathway; and moving the zones together along the pathway
toward the second end at a forward wave velocity, and then
toward the first end at a backward wave velocity, so that the major portion of the target chemical constituent is conveyed to the second end.

7. A method of concentrating a target chemical constituent from a mixture of components said mixture constituting a solid, the method comprising the following steps:

providing a pathway over which components are free to move, the pathway having first and second ends;

controlling temperature so as to create consecutive warmer and cooler zones along the pathway;

supplying the mixture of components to the pathway; and moving the zones together along the pathway
toward the second end at a forward wave velocity, and then
toward the first end at a backward wave velocity, so that the major portion of the target chemical constituent is conveyed to the second end.

8. A method of concentrating a target chemical constituent from a mixture of components, the method comprising the following steps:

providing a pathway over which components are free to move, the pathway having first and second ends;

controlling temperature so as to create consecutive warmer and cooler zones along the pathway;

supplying the mixture of components to the pathway; and moving the zones together along the pathway
toward the second end at a forward wave velocity, and then
toward the first end at a backward wave velocity, so that the major portion of the target chemical constituent to the second end, and sensing the target chemical constituent is conveyed that is conveyed to the second end.

9. The method of claim 6 wherein an ion-mobility spectrometer senses the target chemical constituent.

10. The method of claim 2 wherein the forward wave velocity is several times the Soret velocity.

11. The method of claim 2 wherein the backward wave velocity is less than half the Soret velocity.

12. An apparatus for concentrating a target chemical constituent from a mixture of components, the apparatus comprising:

a pathway over which components are free to move, the pathway having first and second ends;

a temperature control system configured to control temperature so as to create a series comprising a plurality of consecutive alternating warmer and cooler zones along the pathway and to displace the series along the pathway so as to move the zones together along the pathway
toward the second end at a forward wave velocity, and then
toward the first end at a backward wave velocity, so that the major portion of the target chemical constituent is conveyed to the second end.

13. An apparatus for concentrating a target chemical constituent from a mixture of components, the apparatus comprising:

a pathway over which components are free to move, the pathway having first and second ends;

a temperature control system comprising resistive heating elements lithographically defined on the interior surface of at least one of the two members and configured to control temperature so as to create consecutive warmer and cooler zones, along the pathway, and to move the zones together along the pathway
toward the second end at a forward wave velocity, and then
toward the first end at a backward wave velocity, so that the major portion of the target chemical constituent is conveyed to the second end.

14. The apparatus of claim 13 wherein the resistive heating elements each have a dimension less than 100 $\mu$m along the pathway.

15. The apparatus of claim 13 wherein the resistive heating elements each have a dimension less than 50 $\mu$m along the pathway.

16. The apparatus of claim 13 wherein the resistive heating elements each have a dimension less than 20 $\mu$m along the pathway.

17. An apparatus for concentrating a target chemical constituent from a mixture of components, the apparatus comprising:

a pathway over which components are free to move, the pathway having first and second ends, said pathway comprising a relatively narrow passage and a relatively wide inlet area at said first end;

a temperature control system configured to control temperature so as to create consecutive warmer and cooler zones along the pathway, and to move the zones together along the pathway
toward the second end at a forward wave velocity, and then
toward the first end at a backward wave velocity, so that the major portion of the target chemical constituent is conveyed to the second end.

18. The apparatus of claim 17 wherein the temperature control system is configured to create a passage thermal profile in the passage and an inlet thermal profile in the inlet area, the passage thermal profile being distinct from the inlet thermal profile.

19. The apparatus of claim 17 wherein the temperature control system is configured to move a thermal profile, comprising consecutive warmer and cooler zones, along the pathway in the inlet area so as to deliver mixture of components to the passage.

20. An apparatus for concentrating a target chemical constituent from a mixture of components, the apparatus comprising:

a pathway over which components are free to move, the pathway having first and second ends;

a temperature control system configured to control temperature so as to create consecutive warmer and cooler zones along the pathway, and to move the zones together along the pathway
toward the second end at a forward wave velocity, and then
toward the first end at a backward wave velocity, so that the major portion of the target chemical constituent is conveyed to the second end, and a sensing device for receiving sample at the second end and detecting target constituent.

21. The apparatus of claim 20 wherein the sensing device comprises an ion-mobility spectrometer.

22. An apparatus for concentrating a target chemical constituent from a mixture of components, the apparatus comprising:

a pathway over which components are free to move, the pathway having first and second ends and being defined by the two circular members, each member having an interior surface facing the pathway in opposition and wherein the pathway is oriented along the radii of said members;

a temperature control system configured to control temperature so as to create consecutive warmer and cooler zones along the pathway, and to move the zones together along the pathway toward the second end at a forward wave velocity, and then toward the first end at a backward wave velocity, so that the major portion of the target chemical constituent is conveyed to the second end.

23. The apparatus of claim 13 wherein the resistive heating elements form concentric rings.

24. An apparatus for concentrating a target chemical constituent from a mixture of components, the apparatus comprising:

a pathway over which components are free to move, the pathway having first and second ends, and having defined by two members, each member having an interior surface facing the pathway in opposition;

a temperature control system including a plurality of interspersed serpentine resistive heating elements and configured to control temperature so as to create consecutive warmer and cooler zones along the pathway, and to move the zones together along the pathway toward the second end at a forward wave velocity, and then toward the first end at a backward wave velocity, so that the major portion of the target chemical constituent is conveyed to the second end.

25. An apparatus for concentrating a target chemical constituent from a mixture of components, the target constituent having a diffusivity and a Soret velocity and collecting in a cooler region more than in a warmer region, the apparatus comprising:

a. two circular members, each having a circumference and a center, in opposition having interior surfaces defining therebetween a pathway along radii over which components are free to move, the pathway having a first end at the circumferences and a second end at the centers;

b. resistive material patterned on the interior surface at least one of the two members, forming thereon concentric rings having a dimension of less than 50 $\mu$m along the radius; and c. a temperature regulation system configured to provide current to the resistive material so as to create along the pathway consecutive warmer and cooler zones and to move the zones together along the pathway repeatedly
   i. toward the second end at a forward wave velocity greater than the Soret velocity, and then
   ii. toward the first end at a backward wave velocity less than the Soret velocity, transporting at least one component having a smaller diffusivity than that of the target constituent, at a greater rate than the target constituent, so that the major portion of target chemical constituent is conveyed to the second end.

26. An apparatus for concentrating a target chemical constituent from a mixture of components, the target constituent having a diffusivity and a Soret velocity and collecting in a cooler region more than in a warmer region, the apparatus comprising:

a. two circular members, each having a circumference and a center, in opposition having interior surfaces defining therebetween a pathway along radii over which components are free to move, the pathway having a first end at the circumferences and a second end at the centers;

b. resistive material patterned on the interior surface at least one of the two members, forming thereon interspersed serpentine heating elements each having a dimension of less than 50 $\mu$m along the radius; and c. a temperature regulation system configured to provide current to the heating elements so as to create along the pathway consecutive warmer and cooler zones and to move the zones together along the pathway repeatedly
   i. toward the second end at a forward wave velocity greater than the Soret velocity, and then
   ii. toward the first end at a backward wave velocity less than the Soret velocity, transporting at least one component having a smaller diffusivity than that of the target constituent, at a greater rate than the target constituent, so that the major portion of target chemical constituent is conveyed to the second end.

* * * * *